United States Patent [19]

Leighton et al.

[11] Patent Number: 4,707,306
[45] Date of Patent: Nov. 17, 1987

[54] ALPHA-AMINOMETHYLENE PHOSPHONATE BETAINES AND POLYMERS PREPARED THEREWITH

[75] Inventors: John C. Leighton, Flanders; Carmine P. Iovine, Bridgewater, both of N.J.

[73] Assignee: National Starch and Chemical Corporation, Bridgewater, N.J.

[21] Appl. No.: 940,701

[22] Filed: Dec. 11, 1986

[51] Int. Cl.⁴ .............................................. C07F 9/38
[52] U.S. Cl. .............................. 260/501.12; 526/278; 560/222; 260/502.5 E
[58] Field of Search .................... 260/501.12, 502.5 E; 560/222

[56] References Cited

U.S. PATENT DOCUMENTS

| | | | |
|---|---|---|---|
| 2,777,872 | 1/1957 | Shacklett | 260/482 |
| 3,160,632 | 12/1964 | Toy et al. | 260/501.12 |
| 3,288,846 | 11/1966 | Irani et al. | 260/502.5 E |
| 3,723,347 | 3/1973 | Mitchell | 260/502.5 E |
| 3,816,333 | 6/1974 | King et al. | 260/502.5 E |
| 3,969,440 | 7/1976 | Edelson et al. | 560/222 |
| 4,012,440 | 3/1977 | Quinlan | 260/501.12 |
| 4,075,243 | 2/1978 | Quinlan | 260/502.5 E |
| 4,409,151 | 10/1983 | Redmore et al. | 260/502.5 E |
| 4,420,399 | 12/1983 | Redmore | 210/700 |
| 4,604,212 | 8/1986 | Matz | 210/700 |

FOREIGN PATENT DOCUMENTS

| | | | |
|---|---|---|---|
| 7114574 | 5/1972 | Netherlands | 560/222 |
| 1230121 | 4/1971 | United Kingdom | 260/502.5 E |

OTHER PUBLICATIONS

The Direct Synthesis of α-Aminomethylphosphonic Acids. Mannich-Type Reactions with Orthophosphorus Acid, K. Moedritzer and R. R. Irani, J. of Organic Chemistry 31, p. 1603, May 1966.

*Primary Examiner*—J. E. Evans
*Attorney, Agent, or Firm*—Ellen T. Dec; Edwin M. Szala

[57] ABSTRACT

Alpha-aminoethylene phosphonate betaines of the formula

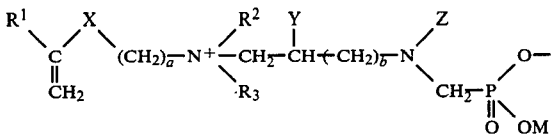

$R^1$ is hydrogen or methyl;
X is

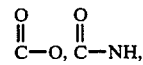

or $CH_2$;
a is 0, 1, 2, or 3, with the condition that when X is

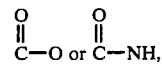

that a be greater than 1;
$R^2$ and $R^3$ are independently $C_1$–$C_6$ alkyl, aryl, benzyl, or cyclohexyl;
Y is hydrogen or hydroxyl;
b is 0, 1, 2, or 3;
Z is $C_1$–$C_6$ alkyl, aryl, benzyl, cyclohexyl, or

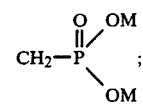

and
M is hydrogen, metallic cation, or ammonium ion are disclosed as are homo- and copolymers thereof.

4 Claims, No Drawings

ALPHA-AMINOMETHYLENE PHOSPHONATE BETAINES AND POLYMERS PREPARED THEREWITH

The present invention relates to alpha-aminomethylene phosphonate betaines and to polymers prepared therewith. In particular, the invention relates to monomers having the general formula:

$$
\begin{array}{c}
R^1 \diagdown \phantom{X} X \phantom{X} \diagup R^2 \phantom{X} Y \phantom{X} \diagup Z \\
\phantom{R^1}C \phantom{XXX} (CH_2)_{\overline{a}} N^+ - CH_2 - CH - (CH_2)_{\overline{b}} N \diagdown \phantom{X} O^- \\
\phantom{RRR}\parallel \phantom{XXXXXXX} \diagdown \phantom{XXXXXXXXXXXXX} CH_2 - P \diagup \\
\phantom{RRRR}CH_2 \phantom{XXXXXXX} R_3 \phantom{XXXXXXXXXXXXXX} \parallel \diagdown OM \\
\phantom{RRRRRRRRRRRRRRRRRRRRRRRRRRRRRRRRRRRRR} O
\end{array}
\quad (I)
$$

$R^1$ is hydrogen or methyl;
X is $$
\overset{O}{\underset{\parallel}{C}}-O, \quad \overset{O}{\underset{\parallel}{C}}-NH,
$$

or $CH_2$;

a is 0, 1, 2, or 3, with the condition that when X is $$
\overset{O}{\underset{\parallel}{C}}-O \text{ or } \overset{O}{\underset{\parallel}{C}}-NH,
$$

that a be greater than 1;

$R^2$ and $R^3$ are independently $C_1$-$C_6$ alkyl, aryl, benzyl, or cyclohexyl;
Y is hydrogen or hydroxyl;
b is 0, 1, 2, or 3;
Z is $C_1$-$C_6$ alkyl, aryl, benzyl, cyclohexyl, or $$
CH_2-P\diagup \overset{O}{\underset{\diagdown OM}{\parallel}} OM ;
$$

and
M is hydrogen, metallic cation, or ammonium ion.

Also disclosed herein are homopolymers of these betaines as well as copolymers thereof prepared with any ethylenically unsaturated copolymerizable comonomer.

These alpha-aminomethylene phosphonate betaines are useful in a variety of applications including soil anti-redeposition agents in detergents, chelating agents for scale inhibition, as crystal modifiers and in oil well drilling needs.

The monomeric betaines are prepared by the reaction of a compound of the general structure $$
\begin{array}{c}
R^1 \diagdown \phantom{X} \diagup R^2 \\
\phantom{R^1}C \phantom{X} X-(CH_2)_a-N \\
\phantom{R^1}\parallel \phantom{XXXXXXXX} \diagdown R^3 \\
\phantom{R^1}CH_2
\end{array}
\quad (II)
$$

where $R^1$, X, a, $R^2$, and $R^3$ are as defined above with compounds of the following general structures:

$$
\begin{array}{c}
\phantom{XX} Y \phantom{XXX} Z \\
L-CH_2-CH-(CH_2)_b-N \diagup \\
\phantom{XXXXXXXXXXXXXXXX}\diagdown CH_2-P \diagup OM \\
\phantom{XXXXXXXXXXXXXXXXXXXXXXXXXX}\parallel \diagdown OM \\
\phantom{XXXXXXXXXXXXXXXXXXXXXXXXXX}O
\end{array}
\quad (III)
$$

or $$
\begin{array}{c}
\phantom{XX}\diagup O \diagdown \phantom{XXX} Z \\
CH_2 \phantom{X}-CH-(CH_2)_b-N \diagup \\
\phantom{XXXXXXXXXXXXXXXX}\diagdown CH_2-P \diagup OM \\
\phantom{XXXXXXXXXXXXXXXXXXXXXXXXXX}\parallel \diagdown OM \\
\phantom{XXXXXXXXXXXXXXXXXXXXXXXXXX}O
\end{array}
\quad (IV)
$$

where L is halogen or $$
\begin{array}{c}
\phantom{X} O \\
\phantom{X} \parallel \\
O-S-R^4 \\
\phantom{X} \parallel \\
\phantom{X} O
\end{array}
$$

with $R^4$ being alkyl or aryl; and Y, b, Z, and M are as defined above.

The reaction of these compounds is carried out in a suitable aqueous solvent (usually water or alcohol/water) at a pH of 7-9 and a temperature of 10°-90° C. Under such conditions the reaction is substantially complete in one-half to ten hours, preferably one to five hours. The solution may be acidified with mineral acid if the acid form of the monomer, (where M is hydrogen), is desired.

If bisphosphonomethylchloroethyl amine is used as the compound of Formula III, the reaction is carried out at a pH of about 7-9 obtained by the addition of sodium hydroxide, preferably pH 8, and a temperature of 20°-60° C., preferably about 50° C. This reaction is carried out under atmospheric pressures and is substantially completed within a period of about 3 hours. Using this starting material, the resulting betaine will correspond to formula I where y is H, Z is —CH$_2$—PO(ONa)$_2$ and b is 0.

In order to produce compounds of formula I where Y is OH, b is 1 or 2, and Z is —CH$_2$—PO(OH)$_2$, chlorohydroxypropyl (or butyl) bisphosphonomethylamine is used as the compound of Formula III and the reaction is carried out at a pH of about 6 to 8, preferably about pH 7, using the same temperature and other conditions described previously.

Isolation of the monomers is difficult owing to their hygroscopic nature. However, these compounds may be isolated by evaporation of the reaction solvent to give a thick syrup. The syrup is then lyophilized to give the monomer in dry form.

Generally, the monomer solution obtained by the above described reaction is used directly in conventional free radical emulsion or solution polymerization procedures. The betaine monomers may be homopolymerized or copolymerized with up to 99% by weight, preferably at least 50% by weight of an ethylenically unsaturated comonomer or mixture of comonomers.

Representative comonomers include acrylic or methacrylic acids and esters thereof with $C_1$-$C_{18}$ alcohols; unsaturated carboxylic acids such as itaconic and maleic acids and esters thereof, (meth)acrylamide and their N-substituted derivatives, such as N-mono and N-dimethyl, -ethyl, -propyl, and -butyl acrylamide or methacrylamide and N-mono or diphenylacrylamide;

vinyl esters such as vinyl acetate or vinyl propionate; vinyl ethers such as butyl vinyl ether; N-vinyl lactams such as N-vinyl pyrrolidinone; halogenated vinyl compounds such as vinyl chloride and vinylidene chloride or fluoride; alkyl vinyl ketones such as methyl or ethyl vinyl ketone; diesters such as dimethyl, diethyl, dipropyl, dibutyl, diphenyl, dibenzyl, and di(phenylethyl) itaconate, maleate, and fumarate; and polyethyleneglycol acrylate or methacrylate or polypropyleneglycol acrylate or methacrylate.

Also useful herein are minor amounts (e.g., 0.01 to about 2%) of multifunctional crosslinking monomers. Representative of suitable crosslinkers are those containing a multiplicity of ethylenically unsaturated units per molecule such as diallyl maleate, triallyl cyanurate, tetraethylene glycol dimethylacrylate, hexa-allyl sucrose, etc.

The polymerization is initiated by a free radical initiator such as peracid or salt thereof, e.g., hydrogen peroxide, sodium peroxide, lithium peroxide, peracetic acid, persulfuric acid or the ammonium and alkali metal salts thereof, e.g. ammonium persulfate, sodium peracetate, lithium persulfate, potassium persulfate, sodium persulfate, t-butyl peracetate, etc. Various azo compounds may also be used, azobisisobutyronitrile, for example. A suitable concentration of the initiator is from 0.05 to 10 weight percent and preferably from 0.1 to 3 weight percent.

The free radical initiator can be used alone and thermally decomposed to release the free radical initiating species or can be used in combination with a suitable reducing agent in a redox couple. The reducing agent is typically an oxidizable sulfur compound such as an alkali metal metabisulfite and pyrosulfite, e.g. sodium metabisulfite.

If emulsion polymerization procedures are employed, the emulsifying agent is generally any of the nonionic oil-in-water surface active agents or mixtures thereof generally employed in emulsion polymerization procedures. When combinations of emulsifying agents are used, it is advantageous to use a relatively hydrophobic emulsifying agent in combination with a relatively hydrophilic agent. The amount of emulsifying agent is generally from about 1 to about 10, preferably from about 2 to about 8, weight percent of the monomers used in the polymerization.

The emulsifier used in the polymerization can also be added, in its entirety, to the initial charge or a portion of the emulsifier, e.g. from 90 to 25 percent thereof, can be added continuously or intermittently during polymerization.

The preferred interpolymerization procedure is a modified batch process wherein the major amounts of some or all the comonomers and emulsifier are charged to the reaction vessel after polymerization has been initiated. In this manner, control over the copolymerization of monomers having widely varied degrees of reactivity can be achieved. It is preferred to add a small portion of the monomer emulsion initially and then the remainder of the monomer emulsion intermittently or continuously over the polymerization period which can be from 0.5 to about 10 hours, preferably from about 1 to about 5 hours.

The resulting polymeric emulsion or solution contains 10 to 80%, preferably about 30 to 60% solids, by weight. It may be used directly or the polymer may be recovered in solid form using the procedure described for isolation of the monomer or well-known spray-drying techniques. Using the above described procedure, the polymer is produced at a yield of at least about 90% conversion.

An alternative method for the production of the betaine polymer involves first the polymerization of the tertiary amine monomer with subsequent quaternization of the polymer with phosphonomethylamine reagent. More specifically, these polymers are synthesized by first polymerizing a monomer of the general structure

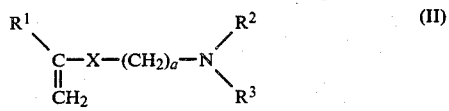

where $R^1$, X, a, $R^2$, and $R^3$ are as defined above to give a homopolymer or, if other ethylenically unsaturated comonomers are used, a copolymer. The resultant polymers can be represented by the general structure:

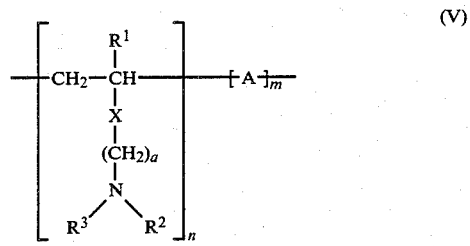

where $R^1$, X, a, $R^2$, and $R^3$ are as previously defined, n and m are positive integers, and A is a repeating unit derived from one or more ethylenically unsaturated comonomers. These polymers are then reacted with a compound of general structure

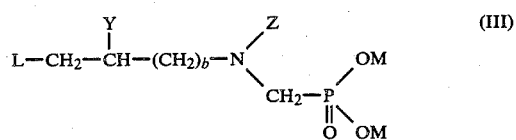

or

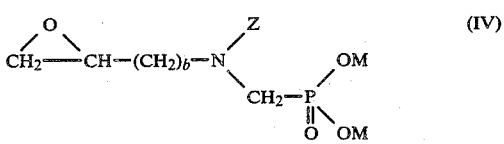

under conditions analogous to those previously described for the monomer preparation.

The resulting derivatized polymers can be represented by the general structure

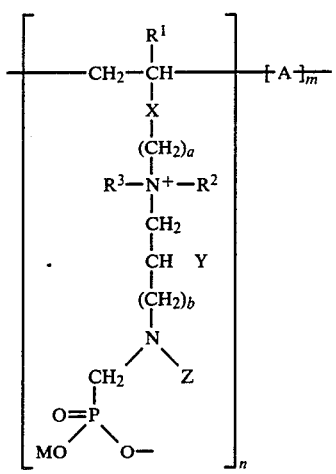

(VI)

where $R^1$, X, a, $R^2$, $R^3$, Y, b, Z, M, n, A, and m are as previously defined. In the latter case, the reagents, reaction conditions and isolation procedures for the quaternization are substantially the same as those described previously however the yields are in the range of about 50 to 70% conversion.

The following examples are presented to illustrate but not to restrict the present invention. Parts and percentages are by weight and temperatures in degrees Celsius unless otherwise noted.

EXAMPLE 1

This example illustrates the preparation of haloalkylaminomethylene diphosphonic acid from haloalkylamines, formaldehyde and phosphorous acid. These acids correspond generally to Formula III where Y is hydrogen, L is chlorine and Z is methylene phosphoic acid. These compounds were made according to the procedure of K. Moedritzer and R. R. Irani, J. Org. Chem. 31 1603 (1966).

A 2 liter flask was equipped with a mechanical stirrer, thermometer, condenser, heating mantle, and addition funnel. Phosphorous acid (164.0 g, 2.0 mol), water (300 ml), and 2-chloroethylamine hydrochloride (115.99 g, 1.0 ml) were charged to the flask, and concentrated hydrochloric acid (300 ml) added. The reaction mixture was brought to reflux and formula solution (324.3 g, 37% solution, 4.0 mol) was added over 1 hour. After the addition was complete the reaction mixture was refluxed an additional 2 hours. The reaction mixture was concentrated to give a thick syrup. Ethanol (275 ml) was added to induce crystallization. The product was filtered and dried to give a white powder. Repetitions of this procedure resulted in yields of 205 to 240 grams (76-90% conversion).

EXAMPLE 2

This example illustrates the preparation of haloalkylaminoalkylmethylenephosphonic acids from N-haloalkyl, N-alkyl amines, formaldehyde, and phosphorous acid. These compounds correspond to Formula III where L is chlorine, Y is hydrogen and Z is methyl. These compounds were made also according to the procedure of K. Moedritzer and R R. Irani, J. Org, Chem 31 1603 (1966).

A 2 liter flask was equipped with a mechanical stirrer, thermometer, condenser heating mantle, and addition funnel. Phosphorous acid (82.2 g, 1.00 mol), N-2-chloroethyl, N-methylamine hydrochloride (130.1 g, 1.0 mol), and water (260 ml) were charged to the flask. Concentrated hydrochloric acid (300 ml) was added slowly. The reaction mixture was heated to reflux and formula solution (159.6 g, 37% solution, 2.0 mol) was added over 1 hour. After the addition was complete, the reaction mixture was held an reflux an additional 2 hours.

As noted by Moedritzer and Irani, crystallization cannot easily be induced. A solution of the product in water (total solution weight 240 g) gave 4.10 meg of organic chloride per gram. Conductometric titration of the product solution yielded three equivalence points, indicating that the product exists as the hydrochloride salt of the aminomethylene phosphonic acid.

EXAMPLE 3

This example describes a two step synthesis for the preparation of halohydroxyalkylaminomethylenediphosphonic acids from alkenylaminomethylenediphosphonic acids, elemental halogen, and water. These compounds correspond to Formula III where L is chlorine, Y is hydroxyl, and Z is $-CH_2-PO(OH)_2$. (It will be recognized by those skilled in the art that during the reaction of the above compounds of Formula III where Y is hydroxyl and L is halogen with the compounds of Formula II, compounds of Formula IV will be produced as intermediates.)

The alkenylaminomethylenediphosphonic acids were synthesized from alkenylamines, formaldehyde, and phosphorous acid in the manner described in the Example 1.

A 500 ml flask was equipped with a mechanical stirrer, condenser, gas dispersion tube, thermometer, and water bath. Allylaminomethylenediphosphonic acid (100. g, 0.408 mol) and water (100 ml) were charged to the flask and partial dissolution occurred. Chlorine gas (31.9 g, 0.449 mol) was bubbled sub-surface into the reaction mixture through the gas dispersion tube. The temperature during the chlorine addition was controlled at 30° C. The resulting solution of 3-chloro-2hydroxypropylaminomethylenediphosphonic acid weighed 240 g and contained 1.7 meg of organic chloride per gram. The solution can be concentrated to yield the product as a white solid, but is generally used directly.

EXAMPLE 4

This example describes the preparation of alpha-aminomethylenephosphonate betaines from reaction of N-dialkylaminoalkyl acrylamides or 2-substituted acrylamides with the haloalkylaminomethylenediphosphonic acids of Example 1. This compound corresponds to one of Formula I where Y is H, Z is $-CH_2-PO(OH)_2$, b is 0, $R_1$, $R_2$ and $R_3$ are $-CH_3$, X is CONH and a is 3.

A 2 liter flask was equipped with a mechanical stirrer, thermometer, condenser, addition funnel, and a pH probe. 2-Chloroethylaminomethylenediphosphonic acid (267.5 g, 1.0 mol) and water (350 ml) were slurried in the reactor. Dimethylaminopropylmethyacrylamide (170.1 g, 1.0 mol) was added portionwise. A solution of sodium hydroxide (120.0 g, 3.0 mol) in $H_2O$ (180 ml) was added to the mixture slowly. The temperature of the reaction mixture was raised to 50° C. and the reaction allowed to continue for 3 hours, at which time analysis for chloride ion indicated that the reaction was substantially complete.

EXAMPLE 5

This example illustrates the preparation of alpha-aminomethylenephosphonate betaines from reaction of N-dialkylaminoalkyl acrylates or 2-substituted acrylates with the halohydroxyalkylaminomethlenediphosphonic acids of Example 3. The resulting monomers correspond to those of Formula I where X is $CO_2$, a is 2, $R_1$, $R_2$, and $R_3$ are —$CH_3$, y is OH, b is 1, and Z is —$CH_2$—$PO(OH)_2$.

A 2 liter flask was equipped with a mechanical stirrer, thermometer, condenser, addition funnel, and a pH probe. 3-Chloro-2-hydroxypropylaminomethylenediphosphonic acid (148.8 g, 0.5 mol) and $H_2O$ (150 ml) were charged to the flask. Dimethylaminoethylmethacrylate (78.5 g, 0.5 mol) was charged to the flask portionwise. A solution of sodium hydroxide (60.0 g, 1.5 mol) in $H_2O$ (90 ml) was added slowly with stirring. The temperature of the reaction mixture was raised to 50° C. and the reaction mixture stirred for 3 hours, at which time analysis for chloride ion indicated that the reaction was substantially complete.

EXAMPLE 6

This example illustrates the copolymerization of the betaine monomer from Example 4 with acrylic acid in aqueous isopropanol.

A 500 ml flask was equipped with a stirrer, condenser, addition funnels, heating mantle, and thermometer. Isopropanol (910 g) and water (88 ml) were charged to the flask and brought to reflux. A monomer charge of acrylic acid (57.6 g) and a 44% solution of the betaine monomer from Example 4 (239.0 g) was added continuously over 3 hours. An initiator charge of sodium persulfate (3.6 g) dissolved in $H_2O$ (16.4 ml) was added simultaneously with the monomer charge over 3 hours. After the additions were complete, the polymer solution was refluxed for 1 hour. The isopropanol was removed by distillation, then the polymer solution was cooled and discharged from the reactor.

This polymer was characterized as follows:
Mw=45,716
Mn=3,571
After exhaustive dialysis against water, the polymer was analyzed for nitrogen and phosphorus content:

|  | Calculated | Observed |
|---|---|---|
| % N | 5.30 | 5.93 |
| % P | 7.85 | 7.01 |

EXAMPLE 7

This example illustrates the copolymerization of betaine monomer from Example 4 with acrylic acid in water with sodium hypophosphite present.

A 2 liter flask was equipped with a stirrer, condensor, addition funnels, heating mantle, nitrogen purge, and thermometer. Water (2.62 ml) and sodium hypophosphite (38.4 g) were charged to the flask and heated to 75° C. A monomer charge of acrylic acid (285. g) and a 30.8% solution of the betaine monomer from Example 4 (62.11 g) was added continuously over 2 hours. Simultaneously, an initiator charge of sodium persulfate (7.5 g) is $H_2O$ (70 ml) was added over 2½ hours. When the initiator addition was complete the reaction temperature was raised to 85° and the reaction mixture stirred for 2 hours. The polymer was then cooled and discharged from the reactor.

This polymer was characterized as follows: Mw=2820; Mn=1280; % P is 3.81 (calculated) and 2.47 (observed).

EXAMPLE 8

This example describes an alternative method for the preparation of polymers containing pendant alpha-aminomethylenephosphonate betaine structures from polymers containing tertiary amines and haloalkylaminomethylenediphosphonic acid.

A tertiary amine-containing polymer is prepared as follows: A 500 ml flask was equipped with a stirrer, condenser, thermometer, addition funnels, and hot water bath. Isopropanol (70 g) and water (110 ml) were added and brought to reflux. A monomer solution of acrylic acid (57.6 g), dimethylaminopropylmethacrylamide (34.0 g), and water (20 ml) were added over 3 hours. Simultaneously, an initiator solution of ammonium persulfate (5. g) in water (25 ml) was added over 3 hours. When the additions were complete, the polymer solution was held at reflux for 1 hour, the isopropanol removed by distillation, then the polymer solution cooled and discharged from the reactor. The polymer concentration was adjusted with water to 40%.

The resulting solution (145.5 g at 40%; 0.120 mole polymeric tertiary amine) was charged to a 500 ml flask equipped with stirrer, thermometer, addition funnel, condenser, and hot water bath. 2-Chloroethylaminomethylenediphosphonic acid (32.1 g, 0.120 mol) was added and the temperature raised to 50° C. Sodium hydroxide (132. g, 3.3 mol) in water 200 ml) was slowly added. The mixture was stirred for 3 hours at 50° C. After exhaustive dialysis against water the polymer was analyzed for phosphorus and nitrogen:

|  | Calculated | Observed |
|---|---|---|
| % N | 4.97 | 5.94 |
| % P | 7.32 | 4.31 |

EXAMPLE 9

This example illustrate the preparation of polymers containing pendant alpha-aminomethylene phosphonate betaine structures from polymers containing tertiary amines and haloalkylaminoalkyl methylene diphosphonic acids in non-aqueous media.

A tertiary amine-containing polymer was prepared as follows: A 2 liter flask was equipped with a stirrer, condenser, thermometer, addition funnels, and hot water bath. Ethanol (180.0 g), benzoyl peroxide (3.0 g), methyl methacrylate (15.0 g) butyl methacrylate (3.0 g), and dimethyl aminopropyl methacrylamide (12.0 g) were charged to the flask and heated to reflux. A monomer solution of methyl methacrylate (135.0 g), butyl methacrylate (27.0 g), dimethylaminopropylmethacrylamide (108.0 g) in ethanol (160.0 g) and an initiator solution of benzoyl peroxide (3.8 g) in ethanol (105.0 g) were added continuously over 4 hours. After the additions were complete, the reaction mixture was held at reflux for an additional 2 hours. A second initiator solution of t-butylperpivalate (2.0 g) in ethanol (30.0 g) was added over ½ hour and the solution was then refluxed an additional hour.

The resulting solution (275 g at 36.3%, 0.235 mole polymeric tertiary amine) was charged to a 1 liter flask equipped with a stirrer, condenser, thermometer, addition funnel, and hot water bath. A solution of N-(2-chloroethyl)-N-methyl-amino methylene phosphosphonic acid (111.9 g at 47.1% in ethanol, 0.235 mol) was added and the reaction mixture heated to 50° C. Ethanolic potassium hydroxide (144.2 g at 25%, 0.642 mole) was added dropwise over 1 hour. The reaction mixture was heated at 50° for 1 hour, then cooled.

The resulting polymer was completely soluble in water, in contrast to the total water insolubility of the parent butyl methacrylate/methyl methacrylate/dimethylaminopropylmethacrylamide polymer. Dialyzed against water, the polymer was analyzed for phosphorus and nitrogen:

|     | Calculated | Observed |
| --- | --- | --- |
| % N | 6.62 | 5.70 |
| % P | 4.89 | 4.33 |

EXAMPLE 10

This example illustrates an emulsion polymerization procedure for the preparation of polymers containing pendant alpha-aminomethylenephosphonate betaine structures.

A 2-L flask is equipped with a stirrer, condenser, thermometer, additional funnels, hot water bath, and nitrogen purge. Ethoxylated nonylphenol (6.9 g), water (192.0 g) and t-butylhydroperoxide (0.06 g) are charged to the flask. The pH of this initial charge is adjusted to 4.0 using acetic acid. With agitation a pre-emulsified mixture of ethyl acrylate (475.0 g), betaine monomer (Example 1, 38%, 132 g), water (55.0 g), ethoxylated nonylphenol (54.5 g), and t-butylhydroperoxide (0.6) is added at 60° over 4 hours. Simultaneously, a solution of sodium formaldehyde sulfoxylate (0.6 g) in water (20 g) is added. The resulting emulsion polymer is coagulated and washed with water. The washed polymer is analyzed for phosphorus content.

|     | Calculated | Observed |
| --- | --- | --- |
| % P | 1.0 | 0.10 |
| % N | 0.44 | 0.05 |

Example 11

This example illustrates the preparation of the betaine analog from dimethylaminopropylmethacrylamide and chloro-hydroxypropyl-bisphosphonomethylamine.

The procedure of Example 5 was repeated using 288 grams of a 51.7% solution of chloro-hydroxypropyl-bisphosphonomethylamine and 85 grams of dimethylaminopropylmethacrylamide with the pH adjusted to 7 with 150 grams of a 40% solution of sodium hydroxide.

The resulting betaine (52.3% solids) was used directly in a polymerization with acrylic acid using the procedure of Example 3 with 144 grams acrylic acid and 533 grams of the betaine solution.

Analysis of the dialyzed polymer gave the following:

|     | Calculated | Observed |
| --- | --- | --- |
| % P | 10.3 | 7.26 |
| % N | 6.21 | 5.57 |

Now that the preferred embodiments of the present invention have been described in detail, various modifications and improvements thereon will become readily apparent to those skilled in the art. Accordingly, the spirit and scope of the present invention is to be limited only by the appended claims, and not by the foregoing disclosure.

We claim:

1. Alpha-aminomethylene phosphonate betaine monomers of the formula:

$$R^1\diagdown_{\underset{\underset{CH_2}{\|}}{C}}\diagup^{X}(CH_2)\overline{_a}N^+\diagdown_{R^3}^{R^2}CH_2-CH(CH_2)\overline{_b}N\diagdown_{CH_2-P\diagup^{O-}_{\|\diagdown}}^{Z}$$

where
R$^1$ is hydrogen or methyl;
X is $$\underset{\|}{\overset{O}{C}}-O, \underset{\|}{\overset{O}{C}}-NH,$$

or CH$_2$;
a is 0, 1, 2, or 3, with the condition that when X is $$\underset{\|}{\overset{O}{C}}-O \text{ or } \underset{\|}{\overset{O}{C}}-NH,$$

that a be greater than 1;
R$^2$ and R$^3$ are independently C$_1$–C$_6$ alkyl, aryl, benzyl, or cyclohexyl;
Y is hydrogen or hydroxyl;
b is 0, 1, 2, or 3;
Z is C$_1$–C$_6$ alkyl, aryl, benzyl, cyclohexyl or $$CH_2-P\diagup^{O}_{\diagdown OM}^{OM}\!\!\!\!\!\!\!\!^{\|};$$

and
M is hydrogen, metallic cation, or ammonium ion.

2. The monomers of claim 1 wherein R$^1$, R$^2$ and R$^3$ are methyl.

3. The monomers of claim 1 wherein X is $$\underset{\|}{\overset{O}{C}}-NH.$$

4. The monomers of claim 1 wherein Z is $$CH_2-\overset{O}{\underset{\|}{P}}-(OM)_2.$$

* * * * *